United States Patent [19]

Richmond et al.

[11] Patent Number: 4,485,048

[45] Date of Patent: Nov. 27, 1984

[54] ETHOXYLATED QUATERNARY BENZYL COMPOUNDS

[75] Inventors: James M. Richmond, Naperville; Keith D. Stanley, Downers Grove, both of Ill.

[73] Assignee: Akzona Incorporated, Enka, N.C.

[21] Appl. No.: 406,413

[22] Filed: Aug. 9, 1982

[51] Int. Cl.³ .............................................. C07F 5/04
[52] U.S. Cl. ................... 260/462 R; 252/8.8; 252/547; 564/287; 564/389; 564/390
[58] Field of Search ................... 260/462 R; 564/287, 564/389, 390; 252/8.8, 547

[56] References Cited

U.S. PATENT DOCUMENTS

| | | | |
|---|---|---|---|
| 3,279,981 | 10/1966 | Geiger et al. | 564/287 X |
| 3,444,200 | 5/1969 | Miller et al. | 564/287 X |
| 3,558,336 | 1/1971 | Baer | 106/165 |
| 3,772,357 | 11/1973 | Hamanaka | 260/462 R X |
| 3,790,606 | 2/1974 | Sellet | 260/401 |
| 3,802,895 | 4/1974 | Dahlgren et al. | 564/389 X |
| 3,809,646 | 5/1974 | Spence | 252/8.8 |
| 3,850,818 | 11/1974 | Katsumi et al. | 252/547 |
| 4,136,039 | 1/1979 | Jäger | 260/462 R |
| 4,264,457 | 4/1981 | Beeks et al. | 252/547 X |
| 4,281,196 | 7/1981 | Rutzen et al. | 252/8.8 |
| 4,376,736 | 3/1983 | Stanley | 260/462 R |
| 4,401,577 | 8/1983 | Richmond | 252/8.8 |

Primary Examiner—Helen M. S. Sneed
Attorney, Agent, or Firm—Francis W. Young; Jack H. Hall

[57] ABSTRACT

Novel compounds having the general formula:

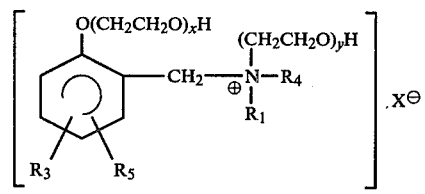

are disclosed, wherein $R_1$ is selected from the group including $C_5$–$C_{22}$ alkyl or alkenyl; $R_3$ and $R_5$ are independently selected from the group including hydrogen or $C_1$–$C_{12}$ alkyl or alkenyl; $R_4$ is either —$(CH_2CH_2O)_zH$, or

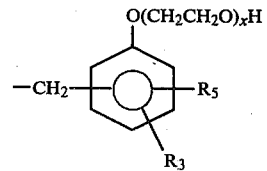

or $C_5$–$C_{22}$ alkyl or alkenyl; x, y, and z are integers of 1 or more and whose sum is between 2 and 15; and $X^\ominus$ is an anion, preferably bis-(ethylene)borate. These ethoxylated quaternary benzyl compounds are useful as fabric softeners.

7 Claims, No Drawings

ETHOXYLATED QUATERNARY BENZYL COMPOUNDS

BACKGROUND OF THE INVENTION

The present invention relates to a new class of compounds, ethoxylated quaternary benzyl compounds, found to be excellent fabric softeners and further found to be particularly useful in organo clay manufacture. For example, organo clays used in the petroleum industry as a drilling mud and to prevent blowback are manufactured by combining a quaternary and a bentonite or hectorite clay. The resulting clay is hydrophobic. A typical quaternary (quat) used in organo clay manufacture is Arquad ®M2HTB quaternary ammonium chloride, a product of the Armak Company, Industrial Chemicals Division, 300 South Wacker Drive, Chicago, Ill. 60606. Arquad ®M2HTB is methyldi(hydrogenatedtallow) benzyl ammonium chloride, 75% active. Isopropyl alcohol (IPA) is required in the manufacture of Arquad ®M2HTB and sold with the quat to the end user, who must remove the IPA prior to organo clay manufacture so that the organo clay will not have a high flash point. Further, because of its chloride anion, the Arquad ®M2HTB used for organo clays imparts to the latter a somewhat corrosive nature.

SUMMARY OF THE INVENTION

The invention is a compound having the general formula:

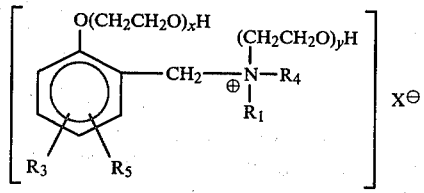

wherein $R_1$ is selected from the $C_5$–$C_{22}$ alkyl or alkenyl groups; $R_3$ and $R_5$ are independently selected from hydrogen or $C_1$–$C_{12}$ alkyl or alkenyl; $R_4$ is either —$(CH_2CH_2O)_zH$, or:

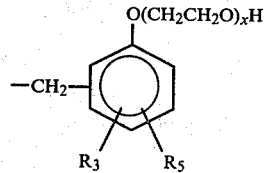

or $C_5$–$C_{22}$ alkyl or alkenyl; x, y, and z are integers of 1 or more and whose sum is between 2 and 15; and $X^\ominus$ is an anion.

Another aspect of the present invention includes the bis-(ethylene) borate anion

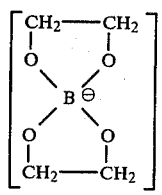

as the preferred anion. The bis-(ethylene) borate anion is less corrosive than many other anions such as chloride and other halogens. In still another aspect of the present invention, $R_1$ and $R_4$ are both long-chain hydrogenated alkyl groups, such as the unsaturated and primarily eighteen-carbon hydrogenated tallow groups. In a still further aspect of the invention, $R_3$ will be either hydrogen, nonyl, methyl or the tertiary butyl group.

An object of the invention is a novel compound that is suitable for softening clothes and fabrics in general. A still further object of the invention is a compound suitable for the manufacture of organo clays; the compound in accordance with the invention will not contain any deleterious substances that may corrode metals contacted by the organo clays, nor any solvents that must be evaporated or in some other way removed during or after organo clay manufacture.

DESCRIPTION OF THE PREFERRED EMBODIMENTS

The manufacture of two compounds in accordance with the present invention is described in these embodiments.

EXAMPLE I

Into a three-neck round bottom flask having a mechanical stirrer, a thermostatically-controlled heating mantle, and a condenser is charged through an addition funnel 234.4 g. (0.467 gram moles) of Armeen ®2HT secondary amine [di(hydrogenatedtallow)amine, $(C_{18}H_{37})_2NH$], a product of the Armak Company, 300 South Wacker Drive, Chicago, Ill. 60606; and 43.9 grams (0.467 gram moles) of phenol. The Armeen ®2HT and phenol are blended and heated to 74° C. 25.5 grams (0.467 gram moles) of methyl formcel (a methanol solution of formaldehyde) are added over approximately five minutes with stirring and the temperature of the reaction mixture is retained at 85° C. for the next 6 hours and 45 minutes, during which time the mixture is continuously stirred. At the end of this period, the heating and stirring of the reaction mixture are ceased, and the mixture is allowed to cool to room temperature. Water and methanol formed in the reaction are stripped off by rotovac, and after over six hours of stripping the analysis of the reaction mixture by thin-layer chromatography indicated a Mannich amine, hydroxybenzyldi(hydrogenatedtallow)amine

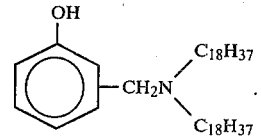

The product has a neutralization equivalent of 609 and contained impurities in the form of primary and secondary amines totalling approximately 6.8% as determined by titration.

214.7 grams (0.353 gram moles) of this Mannich amine product was blended with 3.8 grams (0.0176 gram moles) of sodium methoxide ($CH_3O^\ominus Na^\oplus$) in a 1-liter Parr autoclave having an ethylene oxide reservoir and nitrogen purge line, and heated to about 75° C. over 40 minutes. The reaction mixture was purged twice during that time with nitrogen at 25° C. At the end of the 40 minutes, the mixture was purged once more, and ethylene oxide was added at 35 psig. Thirteen minutes later, after the addition of 0.46 gram moles of ethylene oxide, the addition was halted and the ethylene oxide allowed to digest with the rest of the mixture. After approximately two and one-half hours, the pressure in the autoclave has dropped to approximately 25 psig and the product remaining comprises over 99% of tertiary amine, including 2-(hydroxyethyleneoxy)benzyl di(hydrogenatedtallow)amine

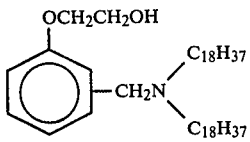

(compound 1436-93) having a neutralization equivalent of 652 and containing impurities in the form of primary and secondary amines totalling approximately 0.8% as determined by titration.

Finally, to 185.7 grams (0.300 gram moles) of tertiary amine 1436-93 are added 23.2 grams (0.375 gram moles) of boric acid ($H_3BO_3$), 10.8 grams (0.600 gram moles) of water, and 18.6 grams of isopropyl alcohol. The components are stirred and heated to 75° C., and the autoclave purged twice with nitrogen at 48 psig. Over the next 8 hours, 2.44 gram moles of ethylene oxide are added in increments and at 48–55 psig, allowing sufficient time between incremental additions so as to permit digestion and sampling the reactor charge within about 1½ hours of each addition. This amount of ethylene oxide represents 8 moles of ethylene oxide per mole of amine. In Table I below, the total moles of ethylene oxide added to the autoclave after each of the four incremental additions are recorded in the first column; the milliequivalents of free amine per gram of reaction mixture is listed in the second column; and the amount of quaternary product in accordance with the invention per gram of reaction mixture is listed in the third column.

TABLE I

| Gram-Moles Ethylene Oxide | Free Amine, meq/gram | Quaternary Product meq/gram |
|---|---|---|
| 1.22 | 0.65 | 0.45 |
| 1.80 | 0.56 | 0.54 |
| 2.14 | 0.19 | 0.73 |
| 2.44 | 0.17 | 0.74 |

The product was identified by thin-layer chromatography and titration as 2-(hydroxyethyleneoxy)benzyl-2-hydroxyethyl di(hydrogenated-tallow) quaternary ammonium bis-(ethylene)borate.

EXAMPLE II

Into a three-neck round bottom flask having a mechanical stirrer, a thermostatically-controlled heating mantle, and a condenser is charged through an addition funnel 242.0 (0.482 gram moles) of Armeen ®2HT secondary amine [di(hydrogenated-tallow)amine, ($C_{18}H_{37})_2NH$], a product of the Armak Company, 300 South Wacker Drive, Chicago, Ill. 60606; and 72.9 grams (0.482 gram moles) of 4-tertiary-butyl phenol. The Armeen ®2HT and t-butyl phenol are blended and heated to 75° C. 26.3 grams (0.482 gram moles) of methyl formcel (a methanol solution of formaldehyde) are added over approximately twelve minutes with stirring and the temperature of the reaction mixture is retained at 85° C. for the next 5 hours and 45 minutes, during which time the mixture is continuously stirred. At the end of this period, the heating and stirring of the reaction mixture are ceased, and the mixture is allowed to cool to room temperature. Water and methanol formed in the reaction are stripped off by rotovac, and after stripping the analysis of the reaction mixture by titration indicates 86.3% tertiary amines, including hydroxy tertiary butyl benzyldi(hydrogenatedtallow)amine

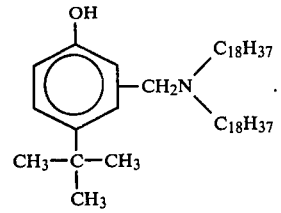

The product had a neutralization equivalent of 681 and contained impurities in the form of primary and secondary amines totalling approximately 8.5% as determined by titration.

248.7 grams (0.365 gram moles) of this Mannich amine product was blended with 3.9 grams (0.018 gram moles) of sodium methoxide ($CH_3O^\ominus Na^\oplus$) in a 1-liter Parr autoclave having an ethylene oxide reservoir and nitrogen purge line, and heated to about 75° C. over 40 minutes. The reaction mixture was purged once during that time with nitrogen at 45 psig, and then a 30 psig head added. The reactor was vented to 0 psig and then charged with 8 psig nitrogen. At the end of the 40 minutes, ethylene oxide was added at 35 psig. Six minutes later, after the addition of 0.49 gram moles of ethylene oxide, the addition was halted and the ethylene oxide allowed to digest into the rest of the mixture. After approximately two and one-half hours, the pressure in the autoclave has dropped to approximately 27 psig and the product remaining comprises over 94% of the tertiary amine 1436-86:

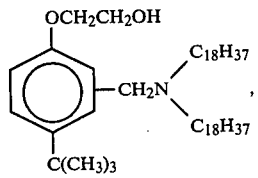

having a neutralization equivalent of 709 and containing impurities in the form of primary and secondary amines totalling approximately 2.5% as determined by titration.

Finally, to 178.1 grams (0.251 gram moles) of tertiary amine 1436-86 are added 19.4 grams (0.314 gram moles) of boric acid ($H_3BO_3$), 9.7 grams (0.157 gram moles) of ethylene glycol, and 17.8 grams of isopropyl alcohol. The components are stirred and heated to 75° C., and the autoclave purged twice with nitrogen at 45 psig and then vented to 8 psig. Over the next 3 hours, 1.0 gram mole of ethylene oxide, or 4 moles of ethylene oxide per mole of amine, was added in increments and at 40–50 psig, allowing sufficient time between incremental additions so as to permit digestion. The reactor charge was sampled during and after completion of the addition. In Table II below, the total moles of ethylene oxide added to the autoclave after each of the two incremental additions are recorded in the first column; the milliequivalents of free amine per gram of reaction mixture is listed in the third column; and the amount of quaternary product in accordance with the invention per gram of reaction mixture is listed in the fourth column.

TABLE II

| Gram-Moles Ethylene Oxide | Time After First Addition of Ethylene Oxide, hours | Free Amine meq/amine | Quat. Product meq/gram |
|---|---|---|---|
| 0.50 | 2:15 | 0.63 | 0.43 |
| 1.0 | 5:00 | 0.49 | 0.54 |
| 1.0 | 7:25 | 0.38 | 0.60 |
| 1.0 | 9:30 | 0.30 | 0.67 |
| 1.0 | 11:25 | 0.30 | 0.67 |

The product was identified as:

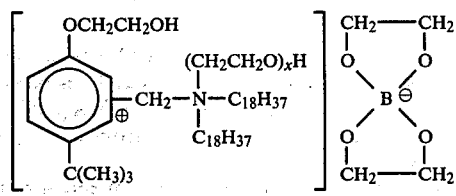

The compounds according to the invention were evaluated for effectiveness as fabric softeners. Terry towels were washed in commercial washers and in rinse water containing one of five softeners of the invention and one control softener on an equal solids concentration basis. The present novel compounds used for testing have the following structures:

1436-95: 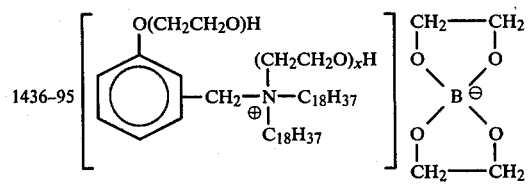

1436-129: 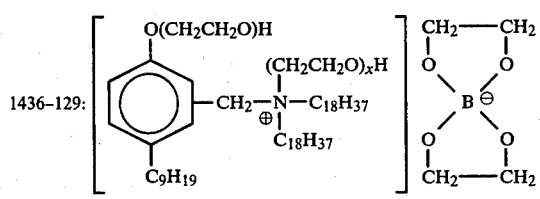

1470-72: 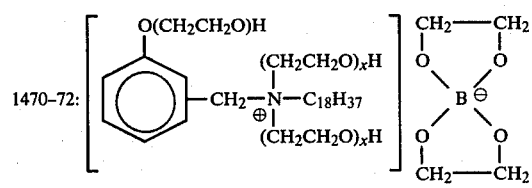

1470-74: 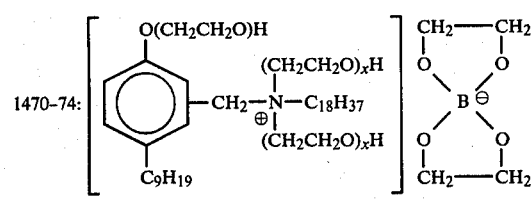

The towels were also washed in Tide ® laundry detergent, a product of Procter and Gamble Co., Cincinnati, Ohio, 45201, without using any softener. The towels were washed once in the machines, tested for softness by a panel, then washed four more times in the machines and again judged by the panel for softness; no additional fabric softener was used in these last four cycles. If a panel member chose a particular towel as being the softest of the three, the corresponding fabric softener was given 1 point. No points were awarded for the two towels not deemed by each of the sixty panel members to be the softest.

A commercial softener, Varisoft ®222-90, a product of the Sherex Chemical Company, Inc., 5777 Frontage Rd., Dublin, Ohio, 43017, was used as a control in these evaluations. The softening formulation contained enough of the commercial softener or the present novel softeners so that the formulation comprised 3% solids. For example, Varisoft 222-90 has a solids content of 90%. To make a formulation comprising 3% solids, 19.98 grams of Varisoft 222-90 were blended with 580.02 grams of water. 110 grams of this 3% formulation was used in each of the evaluation's rinse cycles.

Table III indicates the percent solids in each of the present compounds tested and the amounts of those compounds blended with water to yield 600 grams of a 3% (wt. solids) softening formulation:

TABLE III

| Compound | % Solids | Grams to yield 3% formulation | |
|---|---|---|---|
| | | Compound | Water |
| 1470-72 | 88.7 | 20.28 | 579.72 |
| 1470-74 | 89.4 | 20.13 | 579.87 |
| 1436-129 | 89.2 | 20.18 | 579.82 |
| 1436-95 | 89.5 | 20.11 | 579.89 |
| 1470-134 | 74.1 | 24.29 | 575.71 |

The results of the softener evaluations, indicated in Table IV, demonstrate that the present novel softeners compare very favorably to the known fabric softening compositions in efficacy:

TABLE IV

| | One Application | | | Five Applications | | |
|---|---|---|---|---|---|---|
| Compound | Benzyl Borate | Varisoft | Tide | Benzyl Borate | Varisoft | Tide |
| 1470-72 | 26 | 26 | 8 | 27 | 33 | 0 |
| 1470-74 | 30 | 29 | 1 | 26 | 33 | 1 |
| 1436-129 | 31 | 23 | 6 | 31 | 25 | 4 |
| 1436-95 | 24 | 23 | 13 | 33 | 23 | 4 |

Rewet or wicking is a measure of the absorbency of a fabric. Fabric softeners undesirably lower the absorbency of fabrics; in some cases, repeated treatment of a cotton swatch with a softener can render it nearly waterproof. Rewet measures the height water will climb in a fabric strip suspended vertically over and with one of its ends in a container of water. The higher the rewet, the more absorbent the fabric.

Table V indicates the rewet characteristics after 5, 10, 20, and 30 minutes washed in Varisoft ®222-90, the four compounds of the present invention, and Tide ® laundry detergent, which was used as another control:

TABLE V

| COMPOUND | 5 minutes | 10 minutes | 20 minutes | 30 minutes |
|---|---|---|---|---|
| Varisoft 222-90 | 3.9 | 4.6 | 5.5 | 6.3 |
| 1470-72 | 10.4 | 13.5 | 15.8 | 17.7 |
| 1470-74 | 10.3 | 13.4 | 15.1 | 17.6 |
| 1436-129 | 7.9 | 9.8 | 12.5 | 14.5 |
| 1436-95 | 9.0 | 10.2 | 13.4 | 14.4 |
| Tide | 9.7 | 12.2 | 15.3 | 17.8 |

What is claimed is:

1. A compound having the formula:

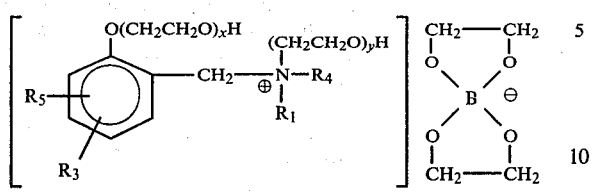

wherein $R_1$ is selected from the group including $C_5$–$C_{22}$ alkyl or alkenyl; $R_3$ and $R_5$ are independently selected from the group including hydrogen or $C_1$–$C_{12}$ alkyl or alkenyl; $R_4$ is either —$(CH_2CH_2O)_zH$, or

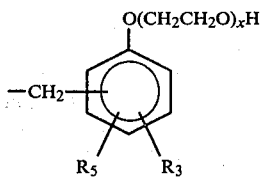

or $C_5$–$C_{22}$ alkyl or alkenyl; and x, y, and z are integers of 1 or more and whose sum is between 2 and 15.

2. The compound set forth in claim 1 wherein $R_1$ and $R_4$ are both hydrogenated tallow groups.

3. The compound set forth in claim 1, wherein $R_3$ is a tertiary butyl group and $R_5$ is hydrogen.

4. The compound set forth in claim 1, wherein $R_3$ and $R_5$ are hydrogen.

5. A compound having the formula:

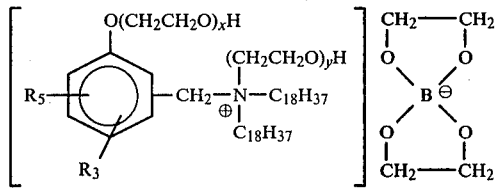

wherein y is an integer between 1 and 13, x is an integer whose value is 1 or more, the sum of x and y is between 2 and 15 and wherein $R_3$ and $R_5$ are independently selected from the group including hydrogen or $C_1$–$C_{12}$ alkyl or alkenyl.

6. The compound set forth in claim 5, wherein $R_3$ and $R_5$ are hydrogen.

7. The compound set forth in claim 5, wherein $R_3$ is the tertiary butyl radical and $R_5$ is hydrogen.

* * * * *